(12) United States Patent
Zhou et al.

(10) Patent No.: US 9,434,947 B2
(45) Date of Patent: Sep. 6, 2016

(54) MODULATION OF KCNH2 ISOFORM EXPRESSION BY OLIGONUCLEOTIDES AS A THERAPEUTIC APPROACH FOR LONG QT SYNDROME

(71) Applicants: Zhengfeng Zhou, Portland, OR (US); Qiuming Gong, Portland, OR (US); Matthew Stump, Portland, OR (US)

(72) Inventors: Zhengfeng Zhou, Portland, OR (US); Qiuming Gong, Portland, OR (US); Matthew Stump, Portland, OR (US)

(73) Assignee: OREGON HEALTH & SCIENCE UNIVERSITY, Portland, OR (US)

( * ) Notice: Subject to any disclaimer, the term of this patent is extended or adjusted under 35 U.S.C. 154(b) by 0 days.

(21) Appl. No.: 14/600,958

(22) Filed: Jan. 20, 2015

(65) Prior Publication Data

US 2016/0208244 A1 Jul. 21, 2016

(51) Int. Cl.
*C12N 15/113* (2010.01)

(52) U.S. Cl.
CPC ......... *C12N 15/113* (2013.01); *C12N 2310/31* (2013.01); *C12N 2310/3233* (2013.01); *C12N 2310/336* (2013.01)

(58) Field of Classification Search
CPC .................................................. C12N 15/113
See application file for complete search history.

(56) References Cited

U.S. PATENT DOCUMENTS

| 6,506,559 B1 * | 1/2003 | Fire ..................... A61K 31/7105 435/325 |
| 2003/0074682 A1 * | 4/2003 | Langheinrich ....... C07K 14/705 800/20 |
| 2005/0245475 A1 * | 11/2005 | Khvorova ............ A61K 31/713 514/44 A |
| 2006/0003322 A1 * | 1/2006 | Bentwich ............. C12N 15/113 435/6.16 |

OTHER PUBLICATIONS

Curran et al. (Cell, vol. 80, pp. 795-803, 1995).*

* cited by examiner

*Primary Examiner* — Jon E Angell
(74) *Attorney, Agent, or Firm* — Jeffrey M. Jackson

(57) ABSTRACT

Oligonucleotides with activity in preventing poly(A) adenylation at intron 9 of the KCNH2 gene, as well as pharmaceutical compositions comprising the oligonucleotides and methods of using the oligonucleotides to treat long QT syndrome in a subject are disclosed. The oligonucleotides include antisense sequences corresponding to sites termed DSE-1 and DSE-2 in intron 9.

7 Claims, 8 Drawing Sheets

SEQUENCE LISTING

<160> NUMBER OF SEQ ID NOS: 6

<210> SEQ ID NO 1
<211> LENGTH: 10
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(4)
<223> OTHER INFORMATION: n is a, c, g, or t

```
<400> SEQUENCE: 1 nnnncaaaac                                                              10

<210> SEQ ID NO 2
<211> LENGTH: 10
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (1)..(4)
<223> OTHER INFORMATION: n is a, c, g, or t

<400> SEQUENCE: 2 nnnnaacaca                                                              10

<210> SEQ ID NO 3
<211> LENGTH: 21
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: misc_feature
<222> LOCATION: (7)..(15)
<223> OTHER INFORMATION: n is a, c, g, t or u

<400> SEQUENCE: 3
aacacannnn nnnnncaaaa c                                                 21

<210> SEQ ID NO 4
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 4
aacacagtag tgaatcaaaa c                                                 21

<210> SEQ ID NO 5
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 5
cagaacacag tagtgaatca aaacc                                             25

<210> SEQ ID NO 6
<211> LENGTH: 26
<212> TYPE: DNA
<213> ORGANISM: Artificial Sequence
<220> FEATURE:
<223> OTHER INFORMATION: Control Oligonucleotide

<400> SEQUENCE: 6
ccaaaactaa gtgatgacac caagac                                            26
```

MODULATION OF KCNH2 ISOFORM EXPRESSION BY OLIGONUCLEOTIDES AS A THERAPEUTIC APPROACH FOR LONG QT SYNDROME

ACKNOWLEDGEMENT OF GOVERNMENT SUPPORT

This invention was made with the support of the United States government under the terms of grant number 2R01 HL68854 awarded by the National Institutes of Health. The United States government has certain rights in this invention.

FIELD

Generally, the field is pharmaceutical compositions, more specifically; the field is pharmaceutical compositions comprising oligonucleotides.

BACKGROUND

KCNH2 or human ether-a-go-go-related gene 1 (hERG1) encodes the Kv11.1 channel that conducts the rapidly activating delayed rectifier K$^+$ current (IKr) in the heart (Warmke J W and Ganetzky B, Proc Natl Acad Sci USA 91, 3438-3442 (1994); Sanguinetti M C et al, Cell 81, 299-307 (1995); Trudeau M C et al, Science 269, 92-95 (1995); and Zhou Z et al, Biophys J 74, 230-241 (1998); all of which are incorporated by reference herein). Kv11.1 channels are essential for cardiac action potential repolarization and mutations in KCNH2 cause long QT syndrome type 2 (LQT2) (Curran M E et al, Cell 80, 795-803 (1995); incorporated by reference herein). Alternative intronic polyadenylation has been shown to direct the expression of two Kv11.1 C-terminal isoforms, the functional Kv11.1a isoform and the non-functional Kv11.1a-USO isoform (Gong Q et al, J Biol Chem 285, 32233-32241 (2010); incorporated by reference herein). Kv11.1a is produced by splicing from exon 9 to exon 10 and use of a distal poly(A) site in exon 15, whereas Kv11.1a-USO is generated by the activation of a proximal poly(A) site within intron 9. The last 359 amino acids of Kv11.1a are absent in Kv11.1a-USO and the truncated isoform fails to form functional channels when expressed in mammalian cells (Kupersmidt S et al, J Biol Chem 273, 27231-27235 (1998); incorporated by reference herein). A novel LQT2 mutation that disrupted the alternative processing of KCNH2 intron 9 and resulted in switching the expression of Kv11.1 isoforms from Kv11.1a to Kv11.1a-USO was reported (Gong Q et al, Circ Cardiovasc Genet 7, 482-490 (2014); incorporated by reference herein). Thus, the relative expression of Kv11.1a and Kv11.1a-USO isoforms plays an important role in the regulation of Kv11.1 channel function and the pathogenesis of LQT2.

The alternative processing of KCNH2 pre-mRNA is regulated by the relative efficiencies of RNA splicing and polyadenylation events. These events depend on interactions between trans-acting splicing and polyadenylation factors and cis-acting elements present in KCNH2. The poly(A) signal within KCNH2 intron 9 consists of a weak, nonca-nonical hexamer, AGUAAA (Gong et al, 2010 supra). When this poly(A) signal is changed to the strong, canonical poly(A) signal, AAUAAA, polyadenylation becomes the dominant reaction, resulting in the predominant expression of Kv11.1a-USO. The elimination of the intron 9 poly(A) signal by the AGUAAA to CGCAAA mutations results in predominant expression of Kv11.1a and an increase in channel current.

SUMMARY

A pharmaceutical composition that acts directly on the poly(A) intron 9 signal of KCNH2 is necessary. One example of such a pharmaceutical composition is an oligonucleotide in an antisense configuration relative to downstream elements of the poly(A) intron 9 signal that facilitate formation of the poly(A) tail.

Disclosed herein are oligonucleotides that include a first sequence of SEQ ID NO: 1 (5'-CAAAAC-3') and a second sequence of SEQ ID NO: 2 (5'-AACACA-3'). The first sequence is the antisense of a site termed DSE-1 herein. The second sequence is the antisense of a site termed DSE-2 herein. In some examples, the oligonucleotide includes both SEQ ID NO: 1 and SEQ ID NO: 2. In still further examples, the oligonucleotide is at least 19 nucleotides in length. In still further examples, the oligonucleotide includes a sequence of SEQ ID NO: 3 (5'-AACACAXXXXXXXXXX-CAAAAC-3') wherein X is any nucleic acid. In additional examples, the oligonucleotide includes a sequence of SEQ ID NO: 4 (5'-AACACAGTAGTGAATCAAAAC-3'). In other examples, the oligonucleotide includes a sequence of SEQ ID NO: 5 (5'-CAGAACACAGTAGTGAAT-CAAAACC-3'). In more examples, the oligonucleotide consists of a sequence that is exactly SEQ ID NO: 5 with no additional sequence.

Additional modifications can be made to any of the disclosed oligonucleotides including the addition of a locked nucleotide, a G-clamp nucleotide, a nucleotide base analog, a 3'-terminal cap moiety, or a phosphate backbone modification. One example of such a modification is the addition of a morpholino oligonucleotide. In still further examples, all the nucleic acids in the oligonucleotide are morpholino oligonucleotides.

Also disclosed are pharmaceutical compositions comprising an effective amount of the morpholino oligonucleotide of any of claims 1-9 and a pharmaceutically acceptable carrier. These pharmaceutical compositions can be for use in treating long-QT syndrome caused by mutations in the KCNH2 gene.

Also disclosed are methods of treating long-QT syndrome caused by mutations in the KCNH2 gene. These methods involve administering to the subject the disclosed pharmaceutical compositions to the subject, thereby treating the long-QT syndrome.

A fully enabling disclosure was made by the inventors in Gong et al, J Mol Cell Cardiol 76, 26-32 (14 Aug. 2014) which is incorporated by reference herein.

SEQUENCE LISTING

Figure 1A:
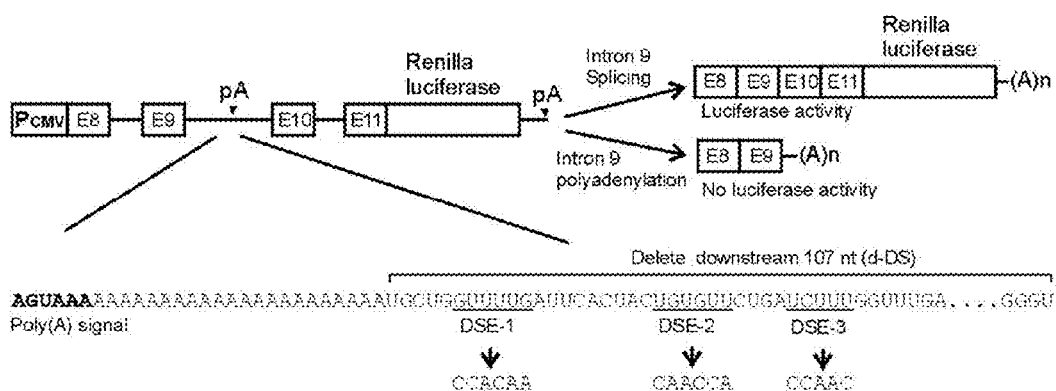
FIG. 1A is a diagram of the KCNH2 minigene luciferase reporter construct described herein and includes the sequence of downstream elements of the KCNH2 intron 9 poly(A) signal. Downstream element deletions and mutations are indicated.

SEQ ID NO: 1 is a sequence that blocks the DSE-1 site of intron 9 of human KCNH2 5'-CAAAAC-3'

SEQ ID NO: 2 is a sequence that blocks the DSE-2 site of intron 9 of human KCNH2 5'-AACACA-3'

SEQ ID NO: 3 is the sequence of an oligonucleotide that blocks both DSE-1 and DSE-2 5'-AACA-CAXXXXXXXXXXCAAAAC-3'

SEQ ID NO: 4 is the sequence of an oligonucleotide that blocks both DSE-1 and DSE-2 5'-AACACAGTAGT-GAATCAAAAC-3'

SEQ ID NO: 5 is the sequence of an oligonucleotide that blocks DSE-1 and DSE-2 of the KCNH2 gene and includes intervening sequence. 5'-CAGAACACAG-TAGTGAATCAAAACC-3'. It is also called Antisense MO or Anti MO herein.

SEQ ID NO: 6 is the sequence of an inverted morpholino oligonucleotide that acts as a negative control. 5'-CCAAAACTAAGTGATGACACCAAGAC-3'. It is also called Invert MO or Inv MO herein.

DETAILED DESCRIPTION

Terms

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." In addition, the materials, methods, and examples are illustrative only and not intended to be limiting.

Administration: To provide or give a subject an agent, such as a composition comprising therapeutic oligonucleotides by any effective route. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes. Binding or stable binding: An association between two substances or molecules, such as the association between an antisense nucleic acid to a sense nucleic acid. Binding can be detected by any procedure known to one skilled in the art, such as by physical or functional properties. For example, binding can be detected functionally by determining whether binding has an observable effect upon a biosynthetic process such as expression of a gene, DNA replication, transcription, translation, protein activity, and the like.

Contacting: Placement in direct physical association, including contacting of a solid with a solid, a liquid with a liquid, a liquid with a solid, or either a liquid or a solid with a cell or tissue, whether in vitro or in vivo. Contacting can occur in vitro with isolated cells or tissue or in vivo by administering to a subject.

Effective amount: An amount of agent, such as an antisense oligonucleotide that is sufficient to generate a desired response, such as reducing or eliminating a sign or symptom of a condition or disease, such as long-QT syndrome. In some examples, an "effective amount" is one that treats (including prophylaxis) one or more symptoms and/or underlying causes of any of a disorder or disease, for example long-QT syndrome. An effective amount can be a therapeutically effective amount, including an amount that prevents one or more signs or symptoms of a particular disease or condition from developing, such as one or more signs or symptoms associated with long-QT syndrome.

Inhibiting or treating a disease: Inhibiting the full development of a disease or condition, for example, in a subject who has or who is at risk for a disease such as long-QT syndrome. "Treatment" refers to any therapeutic intervention that ameliorates a sign or symptom of a disease or pathological condition. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of metastases, an improvement in the overall health or well-being of the subject, or by other clinical or physiological parameters associated with a particular disease. A "prophylactic" treatment is a treatment administered to a subject who does not exhibit signs of a disease or exhibits only early signs for the purpose of decreasing the risk of developing pathology. A "therapeutic" treatment is a treatment administered after the development of significant signs or symptoms of the disease.

Long QT Syndrome: Long QT Syndrome is a heart rhythm disorder that can potentially cause fast, chaotic heartbeats that can trigger fainting or seizures. Long QT can arise as the result of one or more genomic mutations including mutations in the KCNH2 gene.

Mutation: A mutation is any difference in a nucleic acid or polypeptide sequence from a normal, consensus or "wild type" sequence. A mutant is any protein or nucleic acid sequence comprising a mutation. In addition a cell or an organism with a mutation may also be referred to as a mutant.

Some types of mutations include point mutations (differences in individual nucleotides or amino acids); silent mutations (differences in nucleotides that do not result in an amino acid changes); deletions (differences in which one or more nucleotides or amino acids are missing); frameshift mutations (differences in which deletion of a number of nucleotides indivisible by 3 results in an alteration of the amino acid sequence.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237-44, 1988; Higgins & Sharp, CABIOS 5:151-3, 1989; Corpet et al., Nuc. Acids Res. 16:10881-90, 1988; Huang et al. Computer Appls. In the Biosciences 8, 155-65, 1992; and Pearson et al., Meth. Mol. Bio. 24:307-31, 1994. Altschul et al., J. Mol. Biol. 215:403-10, 1990, presents a detailed consideration of sequence alignment methods and homology calculations.

The NCBI Basic Local Alignment Search Tool (BLAST) (Altschul et al., J. Mol. Biol. 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site. BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

Subject: A living multicellular vertebrate organism, a category that includes, for example, mammals and birds. A "mammal" includes both human and non-human mammals, such as mice. In some examples, a subject is a patient, such as a patient diagnosed with long-QT syndrome.

Oligonucleotides

An oligonucleotide may be chemically synthesized. Synthesis of a single stranded nucleic acid makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 micromolar scale protocol with a 2.5 min coupling step for 2T-0-methylated nucleotides. Alternatively, syntheses at the 0.2 micromolar scale can be performed on a 96-well plate synthesizer from Protogene. However, a larger or smaller scale of synthesis is encompassed by the invention, including any method of synthesis now known or yet to be disclosed. Suitable reagents for synthesis of the oligonucleotides disclosed herein are known to those of skill in the art.

A single stranded oligonucleotide can comprise a modified nucleotide. Examples of modified nucleotides include, but are not limited to, nucleotides having a 2'-O-methyl (2'OMe), 2'-deoxy-2'-fluoro (2'F), 2'-deoxy, 5-C-methyl, 2'-O-(2-methoxyethyl) (MOE), 4'-thio, 2'-amino, or 2'-C-allyl group. Modified nucleotides having a conformation such as those described in, for example in Sanger, *Principles of Nucleic Acid Structure*, Springer-Verlag Ed. (1984), are also suitable for use in oligonucleotides. Other modified nucleotides include, without limitation: locked nucleic acid (LNA) nucleotides, G-clamp nucleotides, or nucleotide base analogs. LNA nucleotides include but need not be limited to 2'-O, 4'-C-methylene-(D-ribofuranosyl)nucleotides), 2'-O-(2-methoxyethyl) (MOE) nucleotides, 2'-methyl-thio-ethyl nucleotides, 2'-deoxy-2'-fluoro (2'F) nucleotides, 2'-deoxy-2'-chloro (2Cl) nucleotides, and 2'-azido nucleotides. A G-clamp nucleotide refers to a modified cytosine analog wherein the modifications confer the ability to hydrogen bond both Watson-Crick and Hoogsteen faces of a complementary guanine nucleotide within a duplex (Lin et al, *J Am Chem Soc*, 120, 8531-8532 (1998)). Nucleotide base analogs include for example, C-phenyl, C-naphthyl, other aromatic derivatives, inosine, azole carboxamides, and nitroazole derivatives such as 3-nitropyrrole, 4-nitroindole, 5-nitroindole, and 6-nitroindole (Loakes, *Nucl Acids Res*, 29, 2437-2447 (2001)).

An oligonucleotide may comprise one or more chemical modifications such as terminal cap moieties, phosphate backbone modifications, and the like. Examples of classes of terminal cap moieties include, without limitation, inverted deoxy abasic residues, glyceryl modifications, 4', 5'-methylene nucleotides, 1-(β-D-erythrofuranosyl) nucleotides, 4'-thio nucleotides, carbocyclic nucleotides, 1,5-anhydrohexitol nucleotides, L-nucleotides, -60 -nucleotides, modified base nucleotides, threo pentofuranosyl nucleotides, acyclic 3',4'-seco nucleotides, acyclic 3,4-dihydroxybutyl nucleotides, acyclic 3,5-dihydroxypentyl nucleotides, 3'-3'-inverted nucleotide moieties, 3'-3'-inverted abasic moieties, 3'-2'-inverted nucleotide moieties, 3'-2'-inverted abasic moieties, 5'-5'-inverted nucleotide moieties, 5'-5'-inverted abasic moieties, 3'-5'-inverted deoxy abasic moieties, 5'-aminoalkyl phosphate, 1,3-diamino-2-propyl phosphate, 3-aminopropyl phosphate, 6-aminohexyl phosphate, 1,2-aminododecyl phosphate, hydroxypropyl phosphate, 1,4-butanediol phosphate, 3'-phosphoramidate, 5' phosphoramidate, hexylphosphate, aminohexyl phosphate, 3'-phosphate, 5'-amino, 3'-phosphorothioate, 5'-phosphorothioate, phosphorodithioate, and bridging or nonbridging methylphosphonate or 5'-mercapto moieties (see, e.g., U.S. Pat. No. 5,998,203; Beaucage et al, *Tetrahedron* 49, 1925 (1993)).

Non-limiting examples of phosphate backbone modifications (i.e., resulting in modified internucleotide linkages) include phosphorothioate, phosphorodithioate, methylphosphonate, phosphotriester, morpholino, amidate, carbamate, carboxymethyl, acetamidate, polyamide, sulfonate, sulfonamide, sulfamate, formacetal, thioformacetal, peptide nucleic acid, and alkylsilyl substitutions (see, e.g., Hunziker et al, *Modern Synthetic Methods*, VCH, 331-417 (1995); Mesmaeker et al, *Antisense Research*, ACS, 24-39 (1994); Bennett C F and Swayze E E, *Ann Rev Pharmacol Toxicol* 50, 259-293 (2010); incorporated by reference herein).

Additional examples of modified nucleotides and types of chemical modifications that can be introduced into the modified oligonucleotides of the present invention are described, e.g., in UK Patent No. GB 2,397,818 B and U.S. Patent Publication Nos. 20040192626 and 20050282188.

An oligonucleotide can comprise one or more non-nucleotides. A non-nucleotide may be any subunit, functional group, or other molecular entity capable of being incorporated into a nucleic acid chain in the place of one or more nucleotide units that is not or does not comprise a commonly recognized nucleotide base such as adenosine, guanine, cytosine, uracil, or thymine, such as a sugar or phosphate.

Chemical modification of the oligonucleotide may also comprise attaching a conjugate to the oligonucleotide molecule. The conjugate can be attached at the 5'-and/or the 3'-end of an oligonucleotide via a covalent attachment such as a nucleic acid or non-nucleic acid linker. The conjugate can also be attached to the oligonucleotide through a carbamate group or other linking group (see, e.g., U.S. Patent Publication Nos. 20050074771, 20050043219, and 20050158727). A conjugate may be added to the oligonucleotide for any of a number of purposes. For example, the conjugate may be a molecular entity that facilitates the delivery of the oligonucleotide into a cell or the conjugate a molecule that comprises a drug or label.

Examples of conjugate molecules suitable for attachment to the disclosed oligonucleotides include, without limitation, steroids such as cholesterol, glycols such as polyethylene glycol (PEG), human serum albumin (HSA), fatty acids, carotenoids, terpenes, bile acids, folates (e.g., folic acid, folate analogs and derivatives thereof), sugars (e.g., galactose, galactosamine, N-acetyl galactosamine, glucose, mannose, fructose, fucose, etc.), phospholipids, peptides, ligands for cellular receptors capable of mediating cellular uptake, and combinations thereof (see, e.g., U.S. Patent Publication Nos. 20030130186, 20040110296, and 20040249178; U.S. Pat. No. 6,753,423). Other examples include the lipophilic moiety, vitamin, polymer, peptide, protein, nucleic acid, small molecule, oligosaccharide, carbohydrate cluster, intercalator, minor groove binder, cleaving agent, and cross-linking agent conjugate molecules described in U.S. Patent Publication Nos. 20050119470 and 20050107325. Other examples include the 2'-O-alkyl amine, 2'-O-alkoxyalkyl amine, polyamine, C5-cationic modified pyrimidine, cationic peptide, guanidinium group, amidininium group, cationic amino acid conjugate molecules described in U.S. Patent Publication No. 20050153337. Additional examples of conjugate molecules include a hydrophobic group, a membrane active compound, a cell penetrating compound, a cell targeting signal, an interaction modifier, or a steric stabilizer as described in U.S. Patent Publication No. 20040167090. Further examples include the conjugate molecules described in U.S. Patent Publication No. 20050239739.

The type of conjugate used and the extent of conjugation to the oligonucleotide can be evaluated for improved pharmacokinetic profiles, bioavailability, and/or stability of the oligonucleotide while retaining activity. As such, one skilled in the art in light of this disclosure can screen oligonucleotides having various conjugates attached thereto to identify oligonucleotide conjugates having improved properties using any of a variety of well-known in vitro cell culture or in vivo animal models, such as for long-QT syndrome caused by mutations in the KCNH2 gene.

Morpholino Oligonucleotides

A morpholino oligonucleotide (MO) is a polymeric molecule having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides. The morpholino oligonucleotide instead contains a ring nitrogen with coupling through the ring nitrogen.

Morpholino oligonucleotides are structures from 12 to 25 nucleotides, including a targeting base sequence that is complementary to a target region of a selected preprocessed mRNA such as preprocessed intron 9 of KCNH2. The morpholino antisense oligonucleotide inhibits formation of a poly(A) signal at a site within intron 9 and thereby results in the proper processing of the mRNA to form KCNH2 protein.

The antisense compound employed in the present invention is one that does not activate RNase H. RNase-H active oligomers, of which phosphorothioate oligonucleotides are the most prominent example, operate primarily by a mechanism in which the target mRNA is cleaved. RNase-incompetent oligomers, on the other hand, are believed to act by a steric blocking mechanism. Such compounds include morpholino oligonucleotides, PNA's (peptide nucleic acids), methylphosphonates, and 2'-O-alkyl or -allyl modified oligonucleotides, all of which are known in the art. The morpholino oligonucleotides are composed of morpholino subunits of the form shown in U.S. Pat. Nos. 5,698,685, 5,217,866, 5,142,047, 5,034,506, 5,166,315, 5,521,063, and 5,506,337. The synthesis, structures, and binding characteristics of morpholino oligonucleotides are detailed in these patents so that one of skill in the art in light of this disclosure can create the morpholino oligonucleotides with the sequences disclosed herein.

In a morpholino oligonucleotide, (i) the morpholino groups are linked together by uncharged phosphorus-containing linkages, one to three atoms long, joining the morpholino nitrogen of one subunit to the 5' exocyclic carbon of an adjacent subunit, and (ii) the base attached to the morpholino group is a purine or pyrimidine base-pairing moiety effective to bind, by base-specific hydrogen bonding, to a base in a polynucleotide. The purine or pyrimidine base-pairing moiety is typically adenine, cytosine, guanine, uracil or thymine. Preparation of such oligomers is described in detail in U.S. Pat. No. 5,185,444 (Summerton and Weller, 1993), which is hereby incorporated by reference in its entirety. As shown in the reference, several types of nonionic linkages may be used to construct a morpholino backbone.

Such morpholino oligonucleotides have shown high binding affinity for RNA targets, and the uncharged backbone favors uptake into cells and reduces non-specific binding interactions, relative to charged analogs such as phosphorothioates. They have been shown to provide significantly improved activity and selectivity in inhibiting translation of targeted sequences in comparison to phosphorothioate oligonucleotides. See, for example, Summerton et al., *Antisense & Nucleic Acid Drug Dev.* 7, 63-70, (1997). The morpholino oligonucleotides have very high nuclease resistance and good water solubility, making them good candidates for in vivo use.

The solubility of the morpholino oligonucleotides, and the ability of the compound to resist precipitation on storage in solution, can be further enhanced by derivatizing the oligomer with a solubilizing moiety, such as a hydrophilic oligomer, or a charged moiety, such as a charged amino acid or organic acid. The moiety may be any biocompatible hydrophilic or charged moiety that can be coupled to the antisense compound and that does not interfere with compound binding to the target sequence. The moiety can be chemically attached to the antisense compound, e.g., at its 5' end, by well-known derivatization methods. One preferred moiety is a defined length oligo ethylene glycol moiety, such as triethyleneglycol, coupled covalently to the 5' end of the antisense compound through a carbonate linkage, via a piperazine linking group forming a carbamate linkage with triethyleneglycol, where the second piperazine nitrogen is coupled to the 5'-end phosphorodiamidate linkage of the antisense. Alternatively, or in addition, the compound may be designed to include one a small number of charged backbone linkages, such as a phosphodiester linkage.

The compound is designed to hybridize to the target sequence under physiological conditions with a $T_m$ substantially greater than 37° C., e.g., at least 50° C. and preferably 60° C.-80° C. Although the compound may not be necessarily 100% complementary to the target sequence, so long as it is effective to stably and specifically bind to the target sequence such that formation of a poly(A) at intron 9 is inhibited. The appropriate length of the oligomer to allow stable, effective binding combined with good specificity is about 8 to 40 nucleotide base units, and preferably about 12-25 base units. Mismatches, if present, are less destabilizing toward the end regions of the hybrid duplex than in the middle. Oligomer bases that allow degenerate base pairing with target bases are also contemplated, assuming base-pair specificity with the target and inhibition of poly(A) formation at intron 9 is maintained.

Because morpholino oligonucleotides have bases that are analogs of those of nucleic acids, a description of a morpholino oligonucleotide as having a particular sequence (or a homolog thereof) is a recitation of the structure of the morpholino oligonucleotide.

Chemical modification of the morpholino oligonucleotide can involve attaching a conjugate to the morpholino oligonucleotide. The conjugate can be attached at the 5'- and/or the 3'-end of the sense and/or the antisense strand of the oligonucleotide via a covalent attachment such as a nucleic acid or non-nucleic acid linker. The conjugate can also be attached to the morpholino oligonucleotide through a carbamate group or other linking group (see, e.g., U.S. Patent Publication Nos. 20050074771, 20050043219, and 20050158727). A conjugate can be added to the morpholino oligonucleotide for any of a number of purposes. For example, the conjugate may be a molecular entity that facilitates the delivery of the morpholino oligonucleotide into a cell or the conjugate a molecule that comprises a drug or label.

Examples of conjugate molecules suitable for attachment to a morpholino oligonucleotide include, without limitation, steroids such as cholesterol, glycols such as polyethylene glycol (PEG), human serum albumin (HSA), fatty acids, carotenoids, terpenes, bile acids, folates (e.g., folic acid, folate analogs and derivatives thereof), sugars (e.g., galactose, galactosamine, N-acetyl galactosamine, glucose, mannose, fructose, fucose, etc.), phospholipids, peptides, ligands for cellular receptors capable of mediating cellular uptake, and combinations thereof (see, e.g., U.S. Patent Publication Nos. 20030130186, 20040110296, and 20040249178; U.S. Pat. No. 6,753,423). Other examples include the lipophilic moiety, vitamin, polymer, peptide, protein, nucleic acid, small molecule, oligosaccharide, carbohydrate cluster, intercalator, minor groove binder, cleaving agent, and cross-linking agent conjugate molecules described in U.S. Patent Publication Nos. 20050119470 and 20050107325. Other examples include the 2'-O-alkyl amine, 2'-O-alkoxyalkyl amine, polyamine, C5-cationic modified pyrimidine, cationic peptide, guanidinium group, amidininium group, cationic amino acid conjugate molecules described in U.S. Patent Publication No. 20050153337. Additional examples of conjugate molecules include a hydrophobic group, a membrane active compound, a cell penetrating compound, a cell targeting signal, an interaction modifier, or a steric stabilizer as described in U.S. Patent Publication No. 20040167090. Further examples include the conjugate molecules described in U.S. Patent Publication No. 20050239739.

The type of conjugate used and the extent of conjugation to the morpholino oligonucleotide can be evaluated for improved pharmacokinetic profiles, bioavailability, and/or stability of the morpholino oligonucleotide while retaining activity. As such, one skilled in the art can screen oligonucleotides having various conjugates attached thereto to identify oligonucleotide conjugates having improved properties using any of a variety of well-known in vitro cell culture or in vivo animal models.

Pharmaceutical Compositions

A pharmaceutical composition may be any chemical compound or composition capable of inducing a desired therapeutic or prophylactic effect when properly administered to a subject. A pharmaceutical composition can include a therapeutic agent, a diagnostic agent or a pharmaceutical agent. A therapeutic agent is one that alone or together with one or more additional compounds induces the desired response (such as inducing a therapeutic effect when administered to a subject). In a particular example, a pharmaceutical agent is an agent that significantly reduces one or more symptoms associated with long-QT syndrome. One example is a pharmaceutical composition comprising an oligonucleotide comprising a sequence of SEQ ID NO: 1 and/or a sequence of SEQ ID NO: 2 that is sufficient to block formation of a poly(A) signal in intron 9 of KCNH2.

A pharmaceutically acceptable carrier (interchangeably termed a vehicle) can be any material or molecular entity that facilitates the administration or other delivery of the morpholino oligonucleotides described herein. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In a particular embodiment the carrier is one that allows trafficking of the morpholino oligonucleotide to the heart or one that allows the morpholino oligonucleotide to be taken up by the heart.

An effective amount or concentration of a compound may be any amount of a composition that alone, or together with one or more additional therapeutic agents is sufficient to achieve a desired effect in a subject, or in a cell being treated with the agent. The effective amount of the agent will be dependent on several factors, including, but not limited to, the subject or cells being treated and the manner of administration of the therapeutic composition. In one example, an effective amount or concentration is one that is sufficient to prevent advancement, delay progression, or to cause regression of a disease, or which is capable of reducing symptoms caused by any disease, including long-QT syndrome. In one example, a desired effect is to reduce or inhibit one or more symptoms associated with long-QT syndrome. The one or more symptoms do not have to be completely eliminated for the composition to be effective. For example, a composition can decrease the sign or symptom by a desired amount, for example by at least 20%, at least 50%, at least 80%, at least 90%, at least 95%, at least 98%, or even at least 100%, as compared to the sign or symptom in the absence of the composition. A therapeutically effective amount of a pharmaceutical composition can be administered in a single dose, or in several doses, for example daily, during a course of treatment. However, the therapeutically effective amount can depend on the subject being treated, the severity and type of the condition being treated, and the manner of administration. For example, an effective amount of such agent can vary from about 100 μg -10 mg per kg body weight if administered intravenously.

The actual dosages will vary according to factors such as the particular status of the subject (for example, the subject's age, size, fitness, extent of symptoms, susceptibility factors, and the like) time and route of administration, other drugs or treatments being administered concurrently, as well as the specific pharmacology of treatments for long-QT syndrome for eliciting the desired activity or biological response in the subject. Dosage regimens can be adjusted to provide an optimum prophylactic or therapeutic response.

An effective amount is also one in which any toxic or detrimental side effects of the compound and/or other biologically active agent is outweighed in clinical terms by therapeutically beneficial effects. A non-limiting range for a therapeutically effective amount of treatments for long-QT syndrome within the methods and formulations of the disclosure is about 0.0001 μg/kg body weight to about 10 mg/kg body weight per dose, such as about 0.0001 μg/kg body weight to about 0.001 μg/kg body weight per dose, about 0.001 μg/kg body weight to about 0.01 μg/kg body weight per dose, about 0.01 μg/kg body weight to about 0.1 μg/kg body weight per dose, about 0.1 μg/kg body weight to about 10 μg/kg body weight per dose, about 1 μg/kg body weight to about 100 μg/kg body weight per dose, about 100 μg/kg body weight to about 500 μg/kg body weight per dose, about 500 μg/kg body weight per dose to about 1000 μg/kg body weight per dose, or about 1.0 mg/kg body weight to about 10 mg/kg body weight per dose.

The effective amount can be selected based on the mode of delivery, for example, trans-epidermal, rectal, oral, pulmonary, intranasal delivery, intravenous or subcutaneous delivery.

Determination of effective amount is typically based on animal model studies followed up by human clinical trials and is guided by administration protocols that significantly reduce the occurrence or severity of targeted disease symptoms or conditions in the subject. Suitable models in this regard include, for example, murine, rat, porcine, feline, non-human primate, and other accepted animal model subjects known in the art. Alternatively, effective dosages can be determined using in vitro models (for example, mouse models of long-QT syndrome). Using such models, only ordinary calculations and adjustments are required to determine an appropriate concentration and dose to administer a therapeutically effective amount of the treatments for long-QT syndrome (for example, amounts that are effective to alleviate one or more symptoms of long-QT syndrome).

Treatment of Long-QT Syndrome

Disclosed herein include methods of treating a subject that has or may have long QT syndrome comprising administering a pharmaceutical composition comprising a morpholino oligonucleotide of SEQ ID NO: 1 or a homolog thereof to the subject. The subject may be treated therapeutically or prophylactically.

The administration of pharmaceutical compositions for treatment of long-QT syndrome can be for either prophylactic or therapeutic purposes. When provided prophylactically, the pharmaceutical composition is provided in advance of any clinical symptom of long-QT syndrome. Prophylactic administration serves to prevent or ameliorate any subsequent disease process. When provided therapeutically, the compounds are provided in response to symptoms of the disease. For prophylactic and therapeutic purposes, the pharmaceutical compositions described herein can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol) or as repeated doses within a prolonged prophylaxis or treatment regimen that will yield clinically significant results to alleviate one or more symptoms or detectable conditions associated with long-QT syndrome in the subject.

A subject can be any multi-cellular vertebrate organism, a category that includes human and non-human mammals, such as mice. In some examples a subject is a male. In some examples a subject is a female. Further types of subjects to which the pharmaceutical composition may be properly administered include subjects known to have long-QT syndrome (through, for example, a molecular diagnostic test or clinical diagnosis,) subjects having a predisposition to long-QT syndrome or subjects displaying one or more symptoms of long-QT syndrome.

Administration of the pharmaceutical composition can be by any method of providing or giving a subject a pharmaceutical composition, by any effective route. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes.

Treating a subject encompasses any therapeutic intervention that can ameliorate a sign or symptom of a disease or pathological condition after it has begun to develop, whether or not the subject has developed symptoms of the disease. Ameliorating, with reference to a disease, pathological condition or symptom refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the memory and/or cognitive function of the subject, a qualitative improvement in symptoms observed by a clinician or reported by a patient, or by other parameters well known in the art that are specific to long-QT syndrome.

A symptom may be any subjective evidence of disease or of a subject's condition, for example, such evidence as perceived by the subject; a noticeable change in a subject's condition indicative of some bodily or mental state. A sign may be any abnormality indicative of disease, discoverable on examination or assessment of a subject. A sign is generally an objective indication of disease.

EXAMPLES

The following examples are illustrative of disclosed methods. In light of this disclosure, those of skill in the art will recognize that variations of these examples and other examples of the disclosed method would be possible without undue experimentation.

Example 1

Inhibition of Intronic Polyadenylation with Antisense Morpholino Oligonucleotides Inhibition of cis acting elements in intron 9 of human KCNH2 using antisense morpholino oligonucleotides (MO) results in the further inhibition of Kv11.1a-USO expression, allowing the transcript to be processed to the functional Kv11.1a isoform. Surprisingly, expression of the functional Kv11.1a isoform is upregulated by this antisense oligonucleotide inhibition of KCNH2 intronic polyadenylation.

Generation of a Minigene Luciferase Reporter Construct

A minigene luciferase reporter construct was generated by subcloning the Renilla luciferase gene downstream of a splicing competent KCNH2 minigene comprising KCNH2 genomic DNA from exon 8 to exon 11. The construction of the KCNH2 minigene has been previously described in Gong Q et al, *J Mol Cell Cardiol* 44, 502-509 (2008) which is incorporated by reference herein. The N-terminus of the minigene was Myc tagged. The Myc tag was inserted in-frame with the KCNH2 and luciferase translation sequence. Expression of the minigene luciferase reporter is driven by a CMV promoter. The vector also contains the firefly luciferase gene driven by the SV40 promoter, which was used as a control for transfection efficiency. The deletion and mutations of U/GU-rich elements downstream of the KCNH2 intron 9 poly(A) signal were performed using the pAlter® in vitro mutagenesis system (Promega, Madison, Wis.). HEK293 cells were transiently transfected with the minigene luciferase reporter construct using the Effectene® method (Qiagen, Valencia, Calif). After 24 hours, cells were harvested and assayed for both firefly and Renilla luciferase activity using the Dual-Luciferase assay kit (Promega). Data were analyzed by normalizing Renilla luciferase activity to firefly luciferase activity and presented as mean±SEM.

Generation of a Short KCNH2 Gene and Stable Transfection in Flp-In HEK293 Cells

The generation of a short KCNH2 gene construct, in which the two longest introns, intron 2 (14.9 kb) and intron 5 (4.4 kb), were shortened to 600 by has been previously described (Gong Q et al, Circ Cardiovasc Genet 7, 482-490 (2014); incorporated by reference herein). Mutations were introduced into the short KCNH2 gene by the pAlter® in vitro mutagenesis system. Stably transfected Flp-In HEK293 cells were generated by the co-transfection of the KCNH2 gene constructs (0.1 µg) with the Flp recombinase expression vector pOG44 (0.9 µg) using the Effectene® method and selected with 100 µ/ml hygromycin.

Generation of a Tandem KCNH2 Poly(A) Signal Construct

The generation of a tandem poly(A) signal construct was previously described in Gong Q et al, *J Biol Chem* 285, 32233-32241 (2010); which incorporated by reference herein. The construct contained the SV40 promoter, the firefly luciferase gene, and 308 by of KCNH2 intron 9 followed by a synthetic poly(A) signal. HEK293 cells were transiently transfected with the tandem poly(A) construct as described in Gong et al 2010 supra.

Antisense Morpholino Oligonucleotide Generation and Use

Morpholino oligonucleotides were synthesized by Gene Tools (Philomath, Oreg). The KCNH2 antisense morpholino oligonucleotide was designed to target a 25 nt sequence within KCNH2 intron 9 containing U/GU-rich elements (underlined) essential for the activation of the intron 9 poly(A) signal, 5'-CAG<u>AACACAG</u>TAG<u>TGAAT CAAAACC</u>-3'. An inverted morpholino oligonucleotide with the same sequence but in a reverse orientation was used as a control 5'-CCAAAACTAAGTGATGACACAAGAC-3'. The Endo-Porter® delivery system (Gene Tools) was used to deliver antisense and control morpholino oligonucleotides into the cells.

RNAse Protection Assay

RNA isolation and an RNase protection assay (RPA) were performed as previously described in Gong et al, 2006 supra. Briefly, antisense RNA riboprobes were transcribed in vitro in the presence of biotin-14-CTP. Yeast RNA was used as a control for the complete digestion of the probes by RNase. The relative intensity of each band was quantified using ImageJ® software and adjusted for the number of biotin-labeled cytidines in each protected fragment. The expression level of the hygromycin B resistance gene from the KCNH2 gene constructs was used to normalize the relative expression of Kv11.1 isoforms.

Immunoblot Analysis

Immunoblot analysis was performed as previously described in Gong et al, 2014 supra. The cell lysates were subjected to SDS-polyacrylamide gel electrophoresis and then electrophoretically transferred onto nitrocellulose membranes. The membranes were incubated with an anti-Kv11.1 antibody against the N-terminus of Kv11.1a and Kv11.1a-USO proteins (H-175, Santa Cruz, Santa Cruz, Calif.) at a 1:600 dilution and visualized with the ECL detection kit (Amersham, Piscataway, N.J). The expression level of hygromycin B phosphotransferase (HPH) encoded by hygromycin B resistance gene was used as loading control (Gong et al 2010 supra).

Patch-Clamp Recordings

Membrane currents were recorded in whole cell configuration using suction pipettes as previously described in Zhou et al, 1998 supra. The bath solution contained 137 mM NaCl, 4 mM KCl, 1.8 mM $CaCl_2$, 1 mM $MgCl_2$, 10 mM glucose, and 10 mM HEPES (pH 7.4 with NaOH). The pipette solution contained 130 mM KCl, 1 mM $MgCl_2$, 5 M EGTA, 5 mM MgATP, and 10 mM HEPES (pH 7.2 with KOH). All patch-clamp experiments were performed at 22-23° C. Kv11.1 current was activated by depolarizing steps between −70 and +50 mV from a holding potential of-80 mV and Kv11.1 tail current was recorded following repolarization to −50 mV. The patch-clamp data are presented as mean±SEM and analyzed by Student's t-test. P<0.05 is considered statistically significant.

Figure 1B:
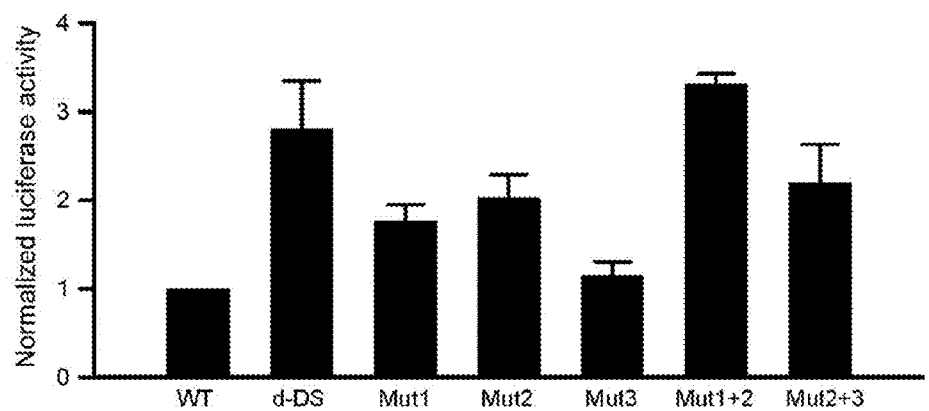
FIG. 1B is a histogram showing the effect of downstream element deletion and mutations on luciferase activity (n=3-6).

Intron 9 Poly(A) Signal Downstream Elements are Required for Kv11.1 Alternative Polyadenylation Polyadenylation sites are primarily defined by a hexameric poly(A) signal AAUAAA or other close variants (Tian B and Manley J L, *Trends Biochem Sci* 38, 312-320 (2013); incorporated by reference herein). In addition to the poly(A) signal, a cis-acting, U/GU-rich downstream element (DSE) is also required for the formation of the poly(A) tail. We have reported that alternative polyadenylation within KCNH2 intron 9 is directed by a noncanonical poly(A) signal AGUAAA (Gong et al 2010 supra). A reporter construct was designed to identify cis-acting elements required for intron 9 polyadenylation by subcloning the *Renilla luciferase* gene downstream of a splicing competent minigene composed of KCNH2 genomic DNA from exon 8 to exon 11. In this reporter construct, the removal of intron 9 generated active luciferase and polyadenylation of intron 9 resulted in no luciferase activity (FIG. 1A). When 107 nucleotides downstream of the poly(A) signal in the minigene luciferase reporter construct were deleted, the deletion significantly increased the luciferase activity (FIG. 1B, d-DS). This indicates that the downstream region contains elements that are required for polyadenylation. Analysis of the intron 9 sequence revealed several putative U/GU-rich elements referred to herein as DSE-1, DSE-2 and DSE-3 (FIG. 1A). DSE-1 was mutated from GUUUUG to CCACAA (Mut1), DSE-2 from UGUGUU to CAACCA (Mut2) and DSE-3 from UCUUU to CCAAC (Mut3) in the minigene luciferase reporter construct. Mut1 and Mut2, but not Mut3, resulted in higher luciferase expression relative to unmutated (FIG. 1B).When both DSE-1 and DSE-2 were mutated (Mut1+2), luciferase expression was higher when compared to Mut1 and Mut2 alone. When both DSE-2 and DSE-3 were mutated (Mut2+3), the luciferase activity was increased, but similar to Mut2 alone. As a result, DSE-1 and DSE-2 are important in KCNH2 intron 9 polyadenylation.

Figure 2A:
FIG. 2A is a diagram of the structure of the short KCNH2 gene construct described herein and includes the sequence of downstream elements of the KCNH2 intron 9 poly(A) signal. DSE-1 and DSE-2 mutations are indicated.
Figure 2B:
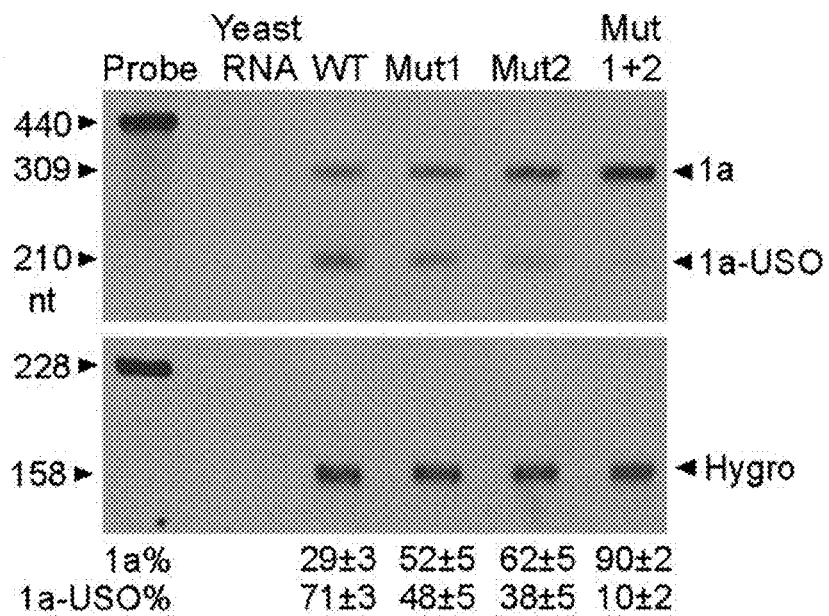
FIG. 2B is an image of a gel resulting from an RNAse protection assay analysis of mRNA in Flp-In HEK293 cells stably expressing WT and DSE mutant short KCNH2 genes. Signals of Kv11.1 isoforms were quantified and shown as a percentage of the total signal (1a+1a-USO) (mean±SD, n=3).
Figure 2C:
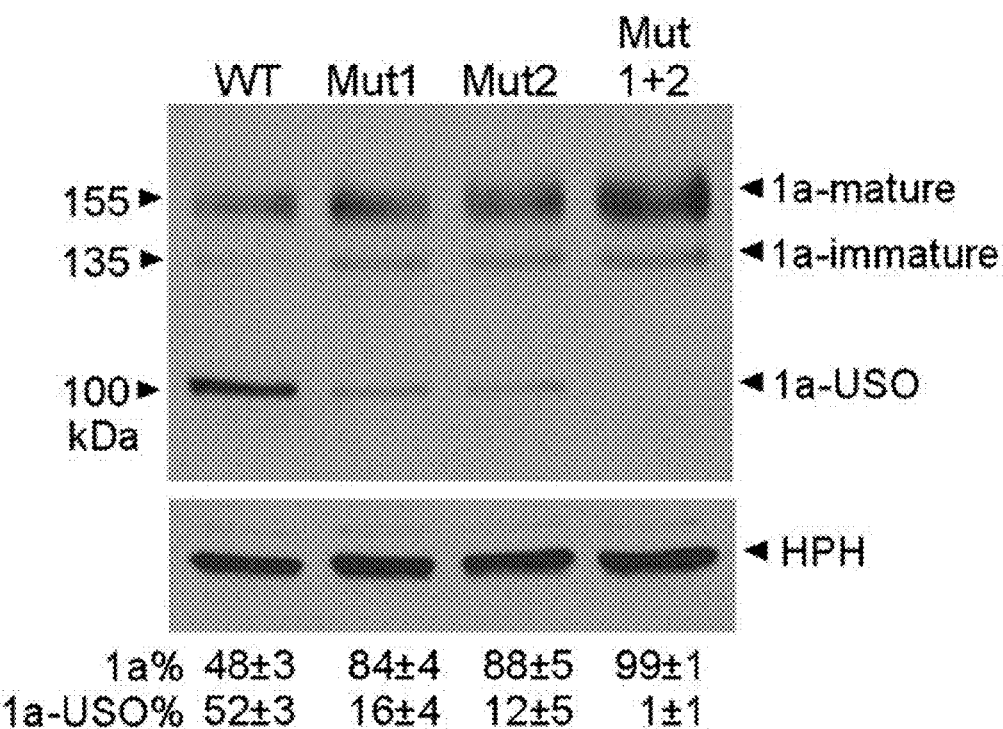
FIG. 2C is an image of a membrane resulting from an immunoblot analysis of Kv11.1 protein expressed in cells expressing WT and DSE mutant short KCNH2 genes. The expression level of hygromycin B phosphotransferase (HPH) encoded by hygromycin B resistant gene served as a loading control. Signals were quantified and shown as isoform percentage of total (1a+1a-USO) Kv11.1 protein (mean±SD, n=3).

Regulation of Kv11.1 Isoform Expression by Intron 9 Poly (A) Signal Downstream Elements To test the effects of the downstream elements in the regulation of Kv11.1 isoform expression, we introduced the DSE-1 and DES-2 mutations into the short KCNH2 gene construct (FIG. 2A). Wild-type (WT) and mutant short gene constructs were stably transfected into Flp-In HEK293 cells. The Mut1 and Mut2 mutations increased Kv11.1a expression and decreased Kv11.1a-USO expression in RPA and immunoblot analyses (FIGS. 2B and 2C).When both DSE-1 and DSE-2 were mutated (Mut1+2) Kv11.1a was predominantly expressed.

Figure 2D:
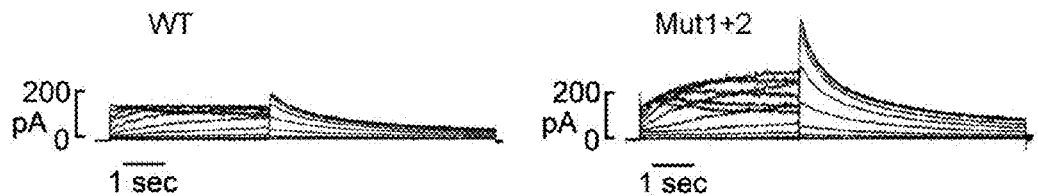
FIG. 2D is a set of two plots showing representative currents recorded from cells stably expressing WT and Mut1+2 short KCNH2 genes.

Patch-clamp studies showed that Kv11.1 channel current was significantly increased in Mut1+2 (FIG. 2D). The maximum tail current densities of WT and Mut1+2 were 7.0±0.6 pA/pF (n=9) and 17.8±1.7 pA/pF (n=10, P<0.001), respectively. These results suggest that DSE-1 and DSE-2 are important downstream elements of the intron 9 poly(A) signal, and that disruption of these elements leads to a shift in KCNH2 pre-mRNA processing toward the production of the Kv11.1a isoform and an increase in Kv11.1 channel function.

Figure 3A:
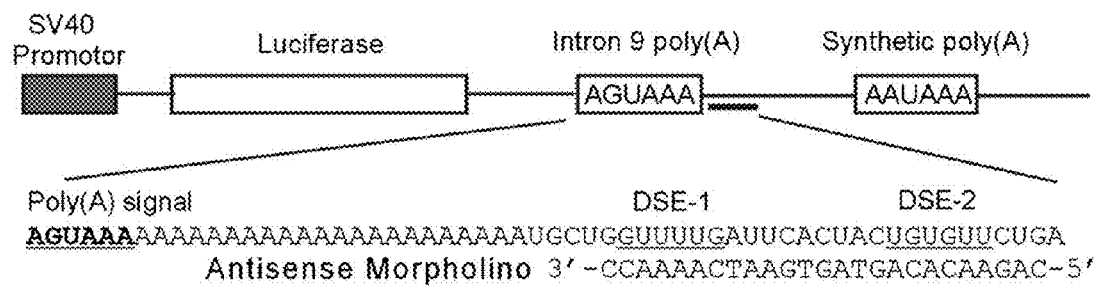
FIG. 3A is a diagram of the tandem poly(A) signal construct and the sequence of a morpholino oligonucleotide that includes SEQ ID NO: 1.

Antisense Morpholino Oligonucleotide Inhibition of the KCNH2 Intron 9 Polyadenylation Because DSE-1 and DSE-2 are important for KCNH2 intron 9 polyadenylation, it was hypothesized that blocking these elements using an antisense oligonucleotide would inhibit KCNH2 intron 9 polyadenylation and lead to the upregulation of the functional Kv11.1a isoform. A 25-mer antisense morpholino oligonucleotide complementary to a sequence comprising the KCNH2 intron 9 downstream elements DSE-1 and DSE-2 (FIG. 3A) was generated. To determine whether the antisense morpholino oligonucleotide could inhibit the poly(A) signal in intron 9, a competition assay using a tandem poly(A) signal construct was performed as described in Gong et al 2010 supra. The KCNH2 intron 9 poly(A) signal AGUAAA and flanking sequences (−130/+172 nt) were positioned upstream of a relatively strong synthetic poly(A) signal (FIG. 3A). Cells expressing the tandem poly(A) construct were treated the with 5 μM negative control or antisense morpholino oligonucleotide of SEQ ID NO: 5. Then an RNAse protection assay was performed using a probe specific to 249 nt of KCNH2 intron 9 (Gong, 2010 supra). Use of the probe results in termination of transcription after generation of a 158 nt fragment, indicating polyadenylation at the intron 9 poly(A) signal and termination of transcription after generation of a 249 nt fragment indicating polyadenylation at the downstream synthetic poly(A) signal.

Figure 3B:
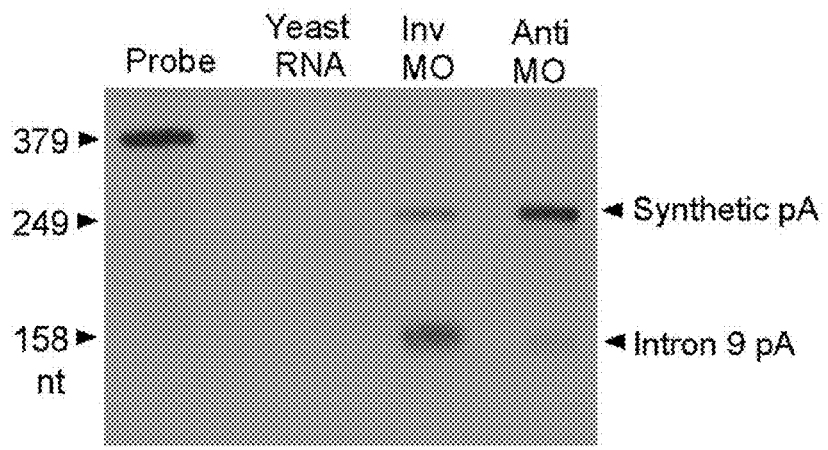
FIG. 3B is an image of a gel resulting from RNAse protection assay analysis of relative usage of intron 9 poly(A) signal and synthetic poly(A) signal following the treatment with invert or antisense MO.
Figure 3C:
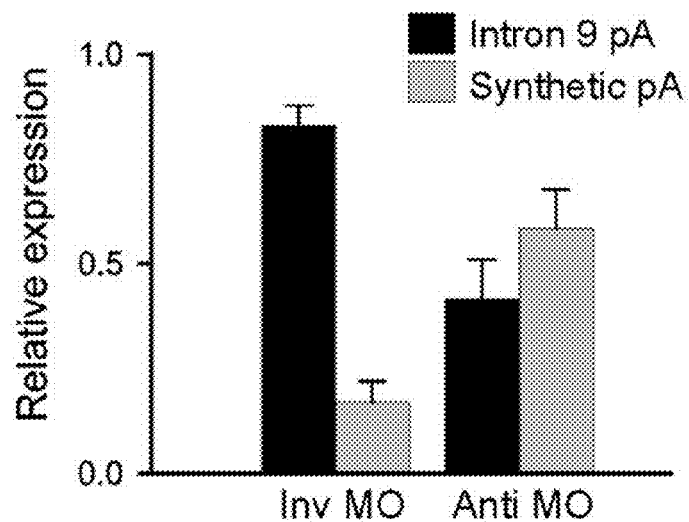
FIG. 3C is a histogram quantifying results of RNAse protection assays as described in FIG. 3B (mean±SD, n=3).

In the presence of the negative control morpholino oligonucleotide of SEQ ID NO: 6, transcription terminated predominantly at the KCNH2 intron 9 poly(A) signal (FIG. 3B). In the presence of the antisense morpholino oligonucleotide of SEQ ID NO: 1 the transcription was predominantly terminated predominantly at the synthetic poly(A) signal. Treatment with the morpholino oligonucleotide of SEQ ID NO: 5 resulted in a 41% usage of the intron 9 poly(A) site relative to 83% usage of the intron 9 poly(A) site in controls (n=3, FIG. 3C). These results show that treatment with the morpholino oligonucleotide of SEQ ID NO: 5 inhibits the poly(A) signal in KCNH2 intron 9.

Modulation of Kv11.1 Isoform Expression by the Antisense Morpholino Oligonucleotide of SEQ ID NO: 1

Figure 4A:
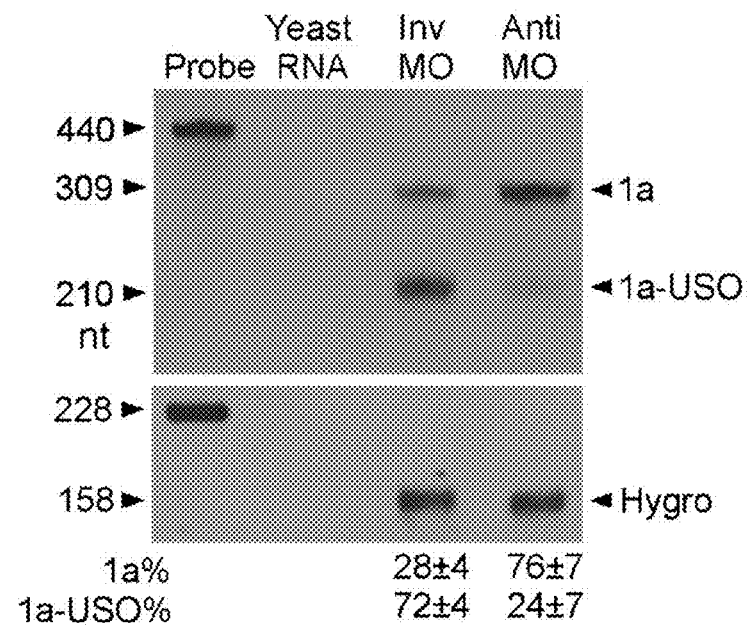
FIG. 4A is an image of a gel resulting from an RNAse protection assay showing the effect of the antisense morpholino oligonucleotide comprising SEQ ID NO: 1 on Kv11.1 isoform expression. Signals were quantified and shown as an isoform percentage of the total signal (1a+1a-USO, mean±SD, n=3).

Flp-In HEK293 stably expressing a short KCNH2 gene were treated with the antisense morpholino oligonucleotide of SEQ ID NO: 1. RNAse protection assays showed that treatment with 5 µM of the antisense morpholino oligonucleotide of SEQ ID NO: 1 for 48 h resulted in greater expression of the Kv11.1a transcript and less expression of the Kv11.1a-USO transcript than the negative control morpholino oligonucleotide (FIG. 4A).

Figure 4B:
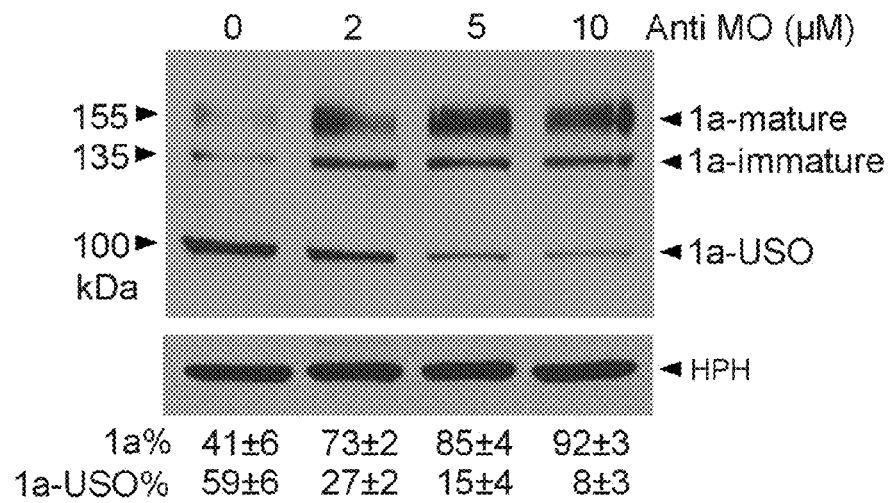
FIG. 4B is an image of an immunoblot analysis showing the concentration dependence of antisense morpholino oligonucleotide comprising SEQ ID NO: 1 on protein expression of Kv11.1 isoforms. Signals were quantified and shown as an isoform percentage of total (1a+1a-USO) Kv11.1 protein (mean±SD, n=3).
Figure 4C:
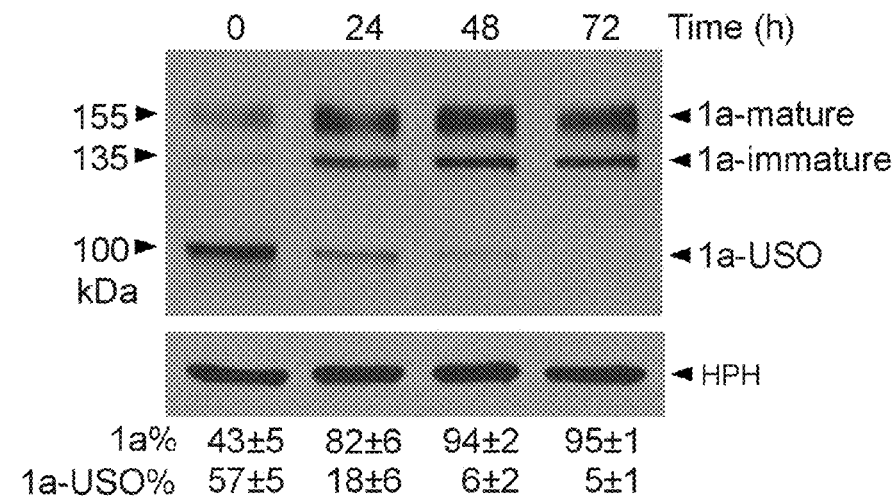
FIG. 4C is an image of an immunoblot showing the effect of treatment with antisense morpholino oligonucleotide comprising SEQ ID NO: 1 on expression of Kv11.1 isoforms for the indicated amounts of time. Signals were quantified and shown as an isoform percentage of total (1a+1a-USO) Kv11.1 protein (mean±SD, n=3).

The effects of the antisense morpholino oligonucleotide of SEQ ID NO: 1 on Kv11.1 protein expression was analyzed by immunoblot. Flp-In HEK293 cells stably expressing the short KCNH2 gene were treated with the indicated concentrations of the antisense morpholino oligonucleotide of SEQ ID NO: 5 for 48 hours or with 5 µM for the indicated amount of time (FIGS. 4B and 4C). Treatment with the antisense morpholino oligonucleotide of SEQ ID NO: 5 resulted in significantly higher expression of Kv11.1a protein and lower expression of Kv11.1a-USO protein relative to controls.

Treatment with the antisense morpholino oligonucleotide exhibited concentration and time dependence. The expression of Kv11.1a protein was higher than the control at a concentration of morpholino oligonucleotide SEQ ID NO: 5 as low as 2 µM with maximal expression at 10 µM (FIG. 4B). The increase in Kv11.1a protein level in cells treated with the morpholino oligonucleotide of SEQ ID NO: 5 relative to controls was observed by 24 hours and reached a maximum by 72 h following antisense MO treatment (FIG. 4C).

Figure 5A:
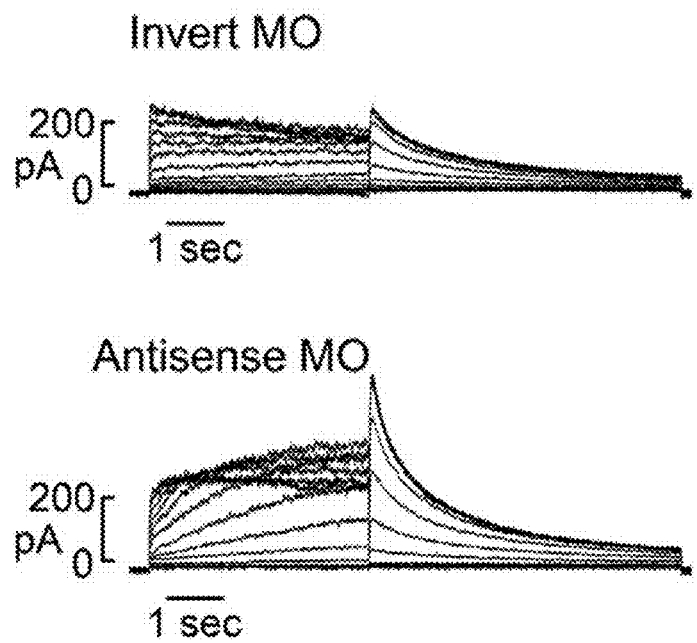
FIG. 5A is a set of two plots showing representative currents recorded from Flp-In HEK293 cells stably expressing short KCNH2 gene following treatment with 10 μM negative control or antisense morpholino oligonucleotide comprising SEQ ID NO: 1 for 48 h.
Figure 5B:
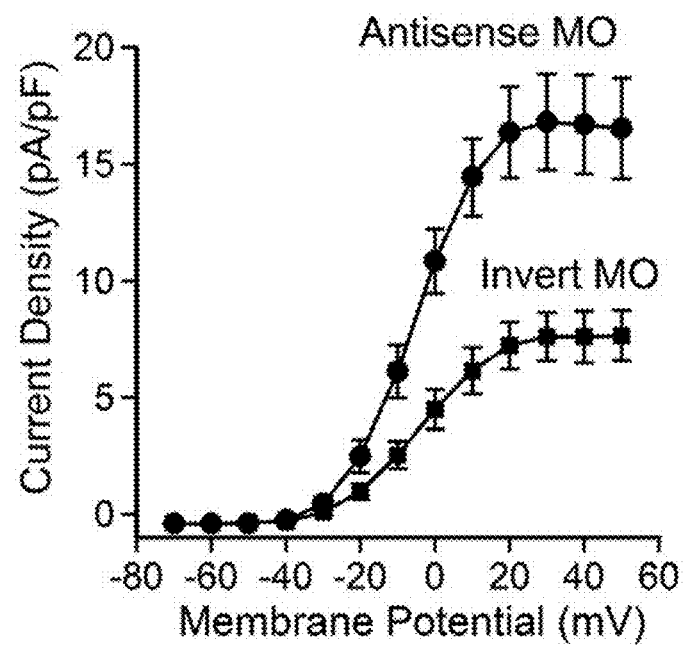
FIG. 5B is an I-V plot of tail current density measured at −50 mV following test voltages from −3 70 to +50 mV for negative control (■) and antisense morpholino oligonucleotide comprising SEQ ID NO: 1 (●).

Treatment with the Antisense Morpholino Oligonucleotide of SEQ ID NO: 1 Resulted in Higher Kv11.1 Channel Current Relative to Controls Patch-clamp recordings of Kv11.1 channel current in cells treated with the antisense morpholino oligonucleotide of SEQ ID NO: 5 were performed. Cells stably expressing the short KCNH2 gene were treated with 10 µM antisense or a negative control morpholino oligonucleotide for 48 hours. Treatment with the antisense morpholino oligonucleotide of SEQ ID NO: 5 significantly increased Kv11.1 channel current compared to the negative control (FIG. 5A). The maximum tail current density in cells treated with the negative control was 7.6±1.0 pA/pF (n =8). The maximum tail current density in cells treated with the antisense morpholino oligonucleotide of SEQ ID NO: 1 was 16.8±2.1 pA/pF (n=9, P<0.001, FIG. 5B).

Figure 5C:
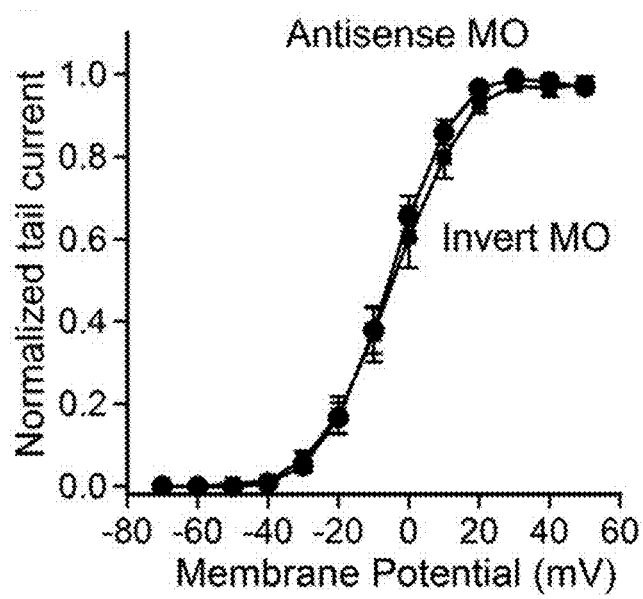
FIG. 5C is a plot of the activation curves for negative control (■) and antisense morpholino oligonucleotide comprising SEQ ID NO: 1 (●).

The voltage dependence of Kv11.1 channel activation was determined by fitting the normalized tail currents with a Boltzmann function (FIG. 5C). The half maximal activation voltages ($V_{1/12}$) in cells treated with the negative control was −4.2±2.9 mV. The half maximal activation voltage in cells treated with antisense morpholino oligonucleotide of SEQ ID NO: 5 was −5.6±2.0 mV. The slope factor (k) in cells treated with the negative control (SEQ ID NO: 6) was 8.7±0.2. The slope factor in cells treated with antisense morpholino oligonucleotide of SEQ ID NO: 5 was 7.9±0.3. These patch-clamp experiments demonstrated that inhibition of polyadenylation of intron 9 using antisense morpholino oligonucleotide of SEQ ID NO: 5 results in higher Kv11.1 channel current.

Figure 6A:
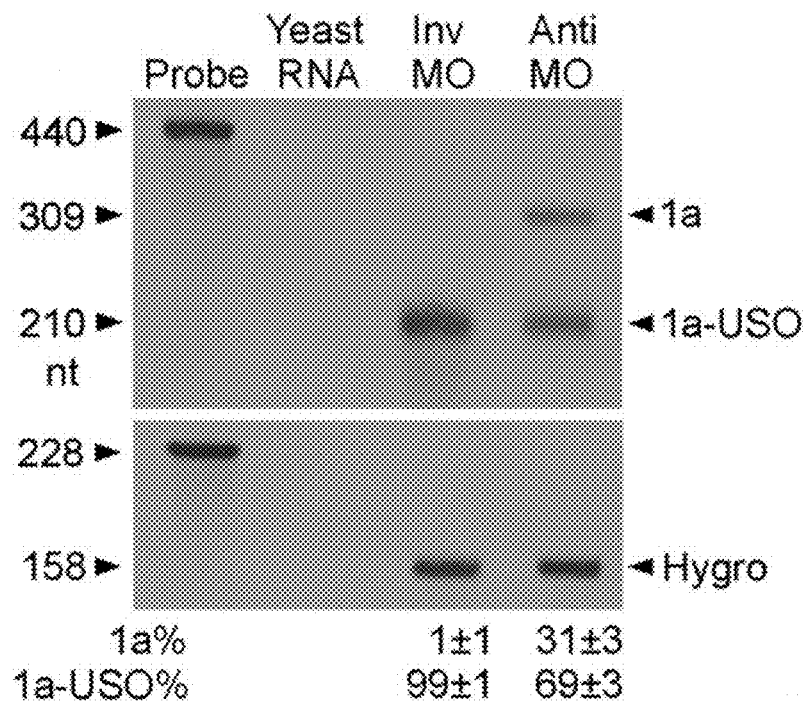
FIG. 6A is an image of a gel resulting from an RNAse protection assay using mRNA from cells stably expressing the short KCNH2 gene containing the canonical poly(A) signal following treatment with 10 μM negative control or antisense morpholino oligonucleotide comprising SEQ ID NO: 1. Signals were quantified and shown as an isoform percentage of the total signal (1a+1a-USO, n=3).

Effect of Antisense MO on Kv11.1 Isoform Expression in Canonical Poly(A) Signal Construct It has been previously shown that the poly(A) signal in KCNH2 intron 9 is intrinsically weak due to the presence of the noncanonical hexamer AGUAAA. When the intron 9 poly(A) signal AGUAAA was changed to the canonical poly(A) signal AAUAAA, the Kv11.1a-USO isoform was predominantly expressed (Gong et al, 2010 supra). To test whether the antisense morpholino oligonucleotide of SEQ ID NO: 5 can mediate the switch of the expression from Kv11.1a-USO to the Kv11.1a isoform in the presence of a strong poly(A) signal, HEK293 cells stably expressing the short KCNH2 gene construct containing a canonical poly(A) signal were treated with negative control (SEQ ID NO: 6) or antisense morpholino oligonucleotide of SEQ ID NO: 5. RNAse protection assay (FIG. 6A), shows that in the presence of the negative control, Kv11.1a-USO was predominantly expressed with no detectable expression of Kv11.1a mRNA. When treated with 10 µM antisense oligonucleotide of SEQ ID NO: 5, the expression of the Kv11.1a isoform was significantly higher.

Figure 6B:
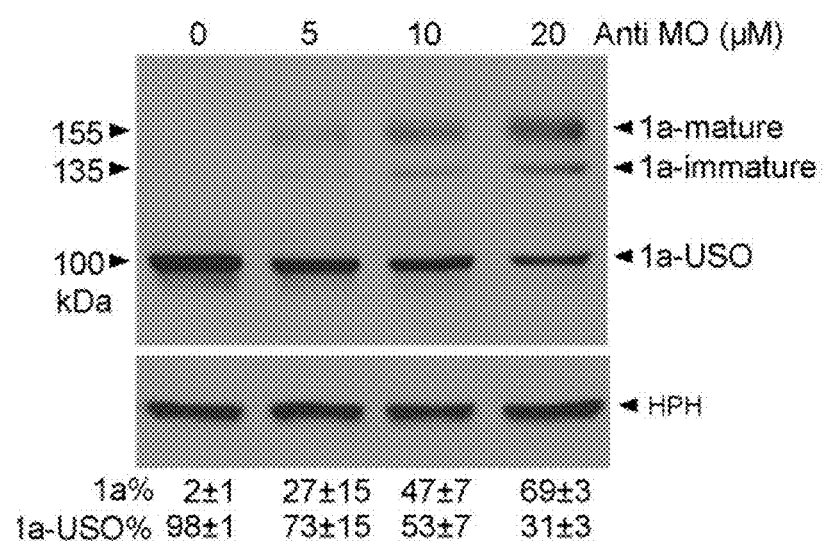
FIG. 6B is an image of an immunoblot analysis showing treatment with antisense morpholino oligonucleotide comprising SEQ ID NO: 1 at the indicated concentrations. Signals were quantified and shown as an isoform percentage of total (1a+1a-USO) Kv11.1 protein (mean±SD, n=3).
Figure 6C:
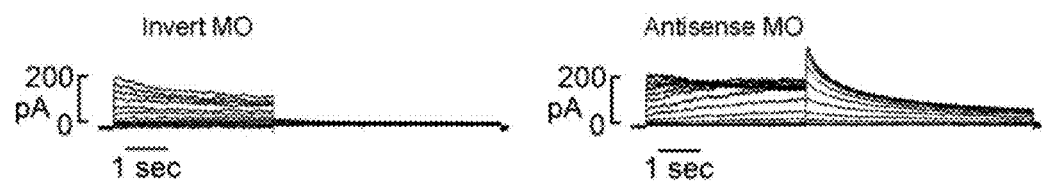
FIG. 6C is a set of two plots showing representative currents recorded from Flp-In HEK293 cells stably expressing short KCNH2 gene containing the canonical poly(A) signal following treatment with 10 μM negative control or antisense morpholino oligonucleotide comprising SEQ ID NO: 1 for 48 h.

Immunoblot analysis revealed that the expression of Kv11.1a protein correlated with treatment with higher concentrations of antisense morpholino oligonucleotide of SEQ ID NO: 5 (FIG. 6B). Patch clamp studies showed that treatment with 10 µM antisense morpholino oligonucleotide of SEQ ID NO: 5 resulted in significantly higher Kv11.1 current than the negative control (FIG. 6C). The maximum tail current densities in cells treated with the negative control (SEQ ID NO: 6) was 1.3±0.3 pA/pF (n=8). The maximum tail current densities in cells treated with the antisense morpholino oligonucleotide of SEQ ID NO: 5 was and 11.5 ±1.4 pA/pF (n=9, P<0.001). This indicates that the antisense morpholino oligonucleotide of SEQ ID NO: 1 can cause a Kv11.1 isoform switch in the presence of a strong intron 9 poly(A) signal.

The invention claimed is:

1. An isolated oligonucleotide comprising SEQ ID NO: 4 that inhibits the formation of a poly(A) signal in intron 9 of KCNH2, wherein the oligonucleotide is no more than 30 nucleotides in length and wherein the oligonucleotide comprises a modified nucleotide, a locked nucleotide, a G-clamp nucleotide, a nucleotide base analog, a 3'-terminal cap moiety, or a phosphate backbone modification.

2. The oligonucleotide of claim 1 comprising SEQ ID NO: 5.

3. The oligonucleotide of claim 2 consisting of a sequence of SEQ ID NO: 5.

4. The oligonucleotide of claim 1 comprising a morpholino nucleotide.

5. The oligonucleotide of claim 4 wherein all of the nucleic acids in the oligonucleotide are morpholino nucleotides.

6. A pharmaceutical composition comprising an effective amount of the oligonucleotide of claim 1 and a pharmaceutically acceptable carrier.

7. A method of treating long-QT syndrome caused by mutations in the KCNH2 gene, the method comprising: administering to the subject the pharmaceutical composition of claim 6, thereby treating the long-QT syndrome.

* * * * *

UNITED STATES PATENT AND TRADEMARK OFFICE
CERTIFICATE OF CORRECTION

| | | |
|---|---|---|
| PATENT NO. | : 9,434,947 B2 | Page 1 of 1 |
| APPLICATION NO. | : 14/600958 | |
| DATED | : September 6, 2016 | |
| INVENTOR(S) | : Zhengfeng Zhou et al. | |

It is certified that error appears in the above-identified patent and that said Letters Patent is hereby corrected as shown below:

At Column 1, Lines 6-13, please delete the following heading and paragraph:
"ACKNOWLEDGEMENT OF GOVERNMENT SUPPORT
This invention was made with the support of the United States government under the terms of grant number HL68854 awarded by the National Institutes of Health. The United States government has certain rights in this invention."

And replace it with the following heading and paragraph:
-- GOVERNMENT SUPPORT
This invention was made with government support under HL068854 awarded by the National Institutes of Health. The government has certain rights in the invention. --

Signed and Sealed this
Ninth Day of July, 2019

Andrei Iancu
*Director of the United States Patent and Trademark Office*